US00PP26920P3

(12) United States Plant Patent
Clark

(10) Patent No.: US PP26,920 P3
(45) Date of Patent: Jul. 12, 2016

(54) PEACH TREE NAMED 'SOUVENIRS'

(50) Latin Name: *Prunus persica*
Varietal Denomination: Souvenirs

(71) Applicant: THE BOARD OF TRUSTEES OF THE UNIVERSITY OF ARKANSAS, Little Rock, AR (US)

(72) Inventor: John Reuben Clark, Fayetteville, AR (US)

(73) Assignee: The Board of Trustees of the University of Arkansas, Little Rock, AR (US)

( * ) Notice: Subject to any disclaimer, the term of this patent is extended or adjusted under 35 U.S.C. 154(b) by 330 days.

(21) Appl. No.: 13/998,203

(22) Filed: Oct. 10, 2013

(65) Prior Publication Data

US 2015/0106983 P1 Apr. 16, 2015

(51) Int. Cl.
*A01H 5/08* (2006.01)

(52) U.S. Cl.
USPC ..... Plt./198
CPC ..... *A01H 5/0868* (2013.01)

(58) Field of Classification Search
USPC ..... Plt./198
CPC ..... A01H 5/0868; A01H 5/0837
See application file for complete search history.

(56) References Cited

U.S. PATENT DOCUMENTS

| | | | |
|---|---|---|---|
| PP86 | P | 2/1934 | Blackburn |
| PP15,159 | P3 | 9/2004 | Clark |
| PP17,742 | P3 | 5/2007 | Clark et al. |

OTHER PUBLICATIONS

Clark, J.R., et al., 'Souvenirs' Peach; Hortscience 48(6): 800-803; 2013.*
Clark, J.R., et al., "'White Diamond' and 'White Cloud' Peaches," HortScience (2011) 46(4):665-667.
Clark, J.R., et al., "'Souvenirs' Peach," (2013) HortScience 48(6):800-803.

* cited by examiner

*Primary Examiner* — Kent L Bell
(74) *Attorney, Agent, or Firm* — Andrus Intellectual Property Law, LLP

(57) ABSTRACT

Description and specification of a new and distinct peach tree cultivar named 'Souvenirs' which originated from a hand-pollinated cross of Ark. 708 (non-patented)×'Winblo' (non-patented) made in 2001. This new peach cultivar can be distinguished by its very firm fruit with slow-melting yellow flesh, early-mid season ripening, medium size, attractive appearance, high red skin color, excellent fruit quality, good flavor, and resistance to bacterial spot disease.

2 Drawing Sheets

Latin name: *Prunus persica.*
Varietal denomination: 'Souvenirs'.

BACKGROUND

A new cultivar of peach tree called 'Souvenirs' is described herein. The new cultivar originated from a hand-pollinated cross of Ark. 708 (non-patented) (female parent)×'Winblo' (non-patented) (male parent) made in 2001. The seeds resulting from this controlled hybridization were germinated in a greenhouse in the late winter 2001/early spring of 2002 and planted in a field near Clarksville, Ark. The seedlings fruited during the summer of 2004 and one seedling, designated Ark. 763, was selected for its very firm fruit with slow-melting yellow flesh, early-mid season ripening, medium size, attractive appearance, high red skin color, excellent fruit quality, good flavor, and resistance to bacterial spot disease.

SUMMARY OF THE INVENTION

The new and distinct cultivar of peach originated from a hand-pollinated cross of Ark. 708 (non-patented, unreleased genotype; female)×'Winblo' (non-patented, public variety; male) made in 2001 near Clarksville, Ark. (West-Central Arkansas).

The seeds resulting from this controlled hybridization were germinated in a greenhouse in the late winter 2001/early spring of 2002 and planted in a field near Clarksville, Ark. The seedlings fruited during the summer of 2004 and one seedling, designated Ark. 763, was selected for its very firm, slow-melting yellow flesh, early-mid season ripening, medium-sized fruits, attractive appearance with high red skin color, excellent fruit quality with good flavor, and resistance to bacterial spot disease.

During 2004, the original plant selection was propagated asexually, at the above-noted location, by budding onto standard peach rootstock cultivar 'Lovell' (non-patented) and a test plot of two plants was established. Subsequently, larger test plantings have been established with asexually multiplied plants at two additional locations in Arkansas (near Clarksville and Hope, Ark.) and at each location propagation was by budding from buds collected at the Clarksville, Ark. test plot. No incompatibility with 'Lovell' peach rootstock has occurred following budding. During all asexual multiplication, the characteristics of the original plant have been maintained and no aberrant phenotypes have appeared.

The new cultivar has been named the 'Souvenirs' cultivar.

BRIEF DESCRIPTION OF THE PHOTOGRAPHS

The accompanying photographs show typical specimens of the new cultivar in color as nearly true as it is reasonably possible to make in a color illustration of this character.

DETAILED DESCRIPTION OF THE NEW CULTIVAR 'SOUVENIRS'

Figure 1:
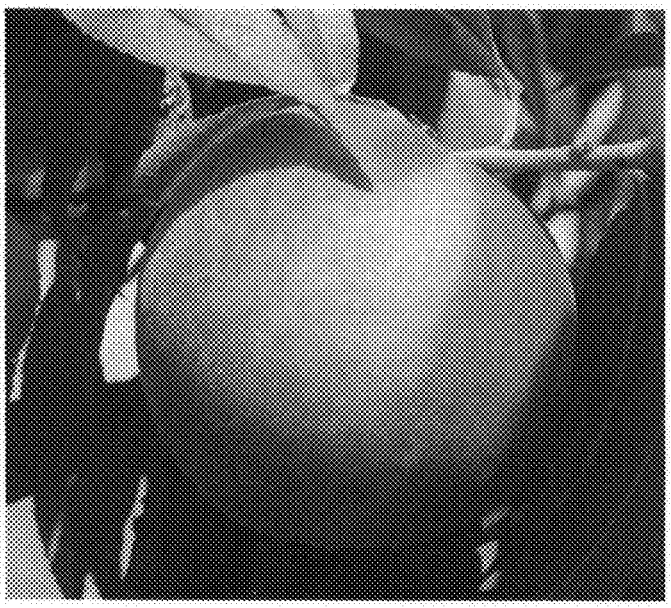
FIG. 1 is a photograph of mature fruit on a tree of 'Souvenirs'.
Figure 2:
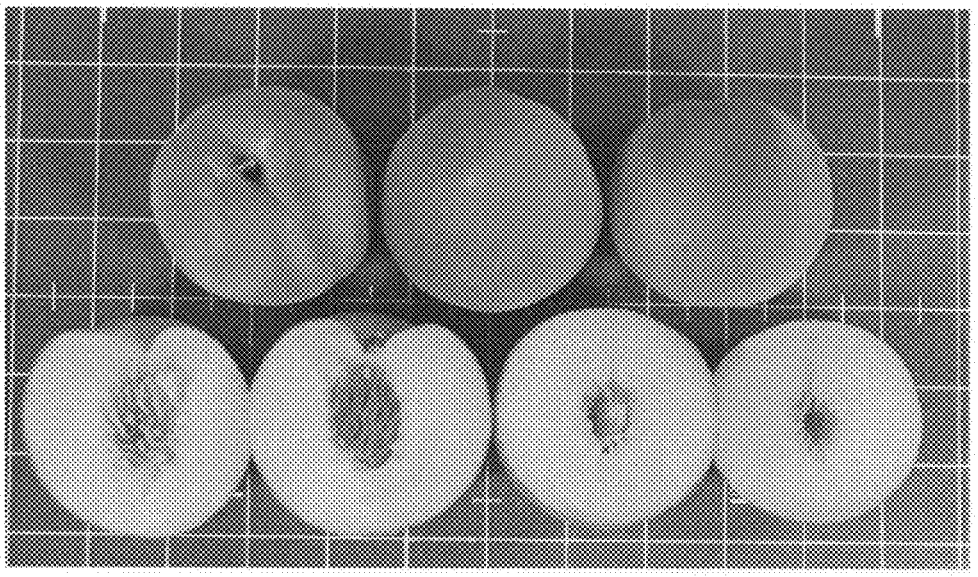
FIG. 2 is a photograph of a whole and longitudinally cut fruit of 'Souvenirs' at maturity.
Figure 3:
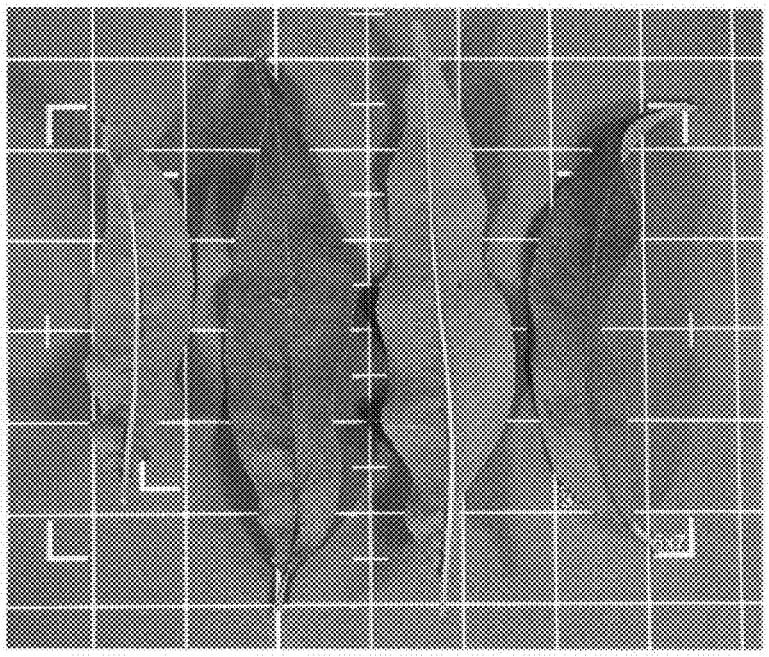
FIG. 3 is a photograph of the adaxial and abaxial sides of mature 'Souvenirs' leaves.

Plants and fruit of this new cultivar differ phenotypically from its parents. The new cultivar is earlier ripening, has flavor, more red skin color, and has more resistance to bacterial spot disease compared to the parent Ark. 708. The new cultivar is different from parent 'Winblo' in that it is low-acid in flavor, ripens earlier, has much firmer flesh and has more resistance to bacterial spot disease. Both the parents and the new cultivar are the genus and species *Prunus persica.*

Trees of the new cultivar are moderately vigorous, productive, standard in size, well-branched and symmetrical with an upright to semi-spreading growth habit, comparable to other peach trees. Trees express a high level of resistance to both foliar and fruit infection of bacterial spot [*Xanthomonas campestris* pv. *pruni* (Smith) Dye] but in some years do not show complete immunity to this disease. The new cultivar blooms in the spring on approximately the same date as 'Loring' (non-patented) and 'White County' (U.S. Plant Pat. No. 17,742). No winter cold injury has been observed on wood or buds of the new cultivar in Arkansas tests where minimum temperatures have reached 5° F. (15° C.) during evaluation. Chilling requirement to break dormancy is estimated to be 800 hours below 45° F. (7° C.).

Fruit of the new cultivar ripens mid-early season, averaging 14 days before 'Loring' and 2 days after 'Redhaven' (non-patented) reference peach cultivars. Average first ripening date is July 6 in west-central Arkansas (Clarksville). Fruit of the new cultivar has not been observed to have split pits, a serious fruit disorder of some peach cultivars. Fruit yields have been good and are comparable to the peach cultivar 'Winblo.'

The fruit is round in shape. Fruits are attractive with an average 90% bright red blush. Fruit finish is good with no blemishes. The fruit skin has light pubescence. The flesh of the fruit is yellow in color and has slight red pigment in the flesh, mostly around the stone or pit. Flesh is melting but very firm until fully mature when it softens, considered a "slow melting" type and firmer at maturity than the 'Loring' or 'Redhaven' reference cultivars. The fruit is a freestone, in that the flesh does not adhere to the pit. Fruit size is medium averaging 183 g.

The fresh fruit rates excellent in flavor. Fruits average 15.3% soluble solids. The flavor is sweet and low-acid with an acidity level of 0.24% malic acid compared to 'Redhaven' with 0.70%.

The following is a detailed description of the botanical and pomological characteristics of the subject peach. Color data are presented in Royal Horticultural Society Colour Chart designations (1986 $2^{nd}$ edition). Where dimensions, sizes, colors and other characteristics are given, it is to be understood that such characteristics are approximations of averages set forth as accurately as practical.

Plants used for botanical data were six years old and grown on a fine sandy loam soil with trickle irrigation near Clarksville, Ark. Trees were trained to an open-center training system and dormant pruned annually. The exception to this is that yield data was collected on trees four years old and trained to a perpendicular V training system. Fruits on all trees were thinned to approximately 6-8 inches between fruits 4-5 weeks after full bloom. The trees were fertilized near budbreak (late March on average) with complete or nitrogen fertilizer. Weeds were controlled with pre- and postemergence herbicides. Routine commercial fungicide and insecticide applications were made to the trees, but no bactericides (for control of bacterial diseases such as bacterial spot disease) were applied. The descriptions reported herein are from specimens grown near Clarksville, Ark.

Plant:

*Size*.—Mature trees (6 years of age) average 3.4 m to 3.7 m in height and 4.8 to 5.9 m in spread or width, and a semi-upright growth habit, as grown on 'Lovell' rootstock using an open-center training system commonly used on peaches. Tree size is comparable to that of the 'Loring' and 'Redhaven' cultivars.

*Growth*.—Vigorous, symmetrical form, good canopy development. Vigor comparable to that of the 'Loring' and 'Redhaven' cultivars.

*Productivity*.—Good productivity and consistent from year to year. Crop load ratings averaged 8.5 on a 10-point scale, higher than 'Loring' with a rating of 7.8. Yield measured 9.1 kg/tree in 2010, for a 2007-planted replicated trial compared to 19.0 kg/tree for 'White County', and 7.1 kg/tree for 'Winblo'.

*Cold hardiness*.—Wood and dormant buds hardy to 5° F. (15° C.), as this was the coldest the trees were exposed to at the test site but hardiness may exceed this temperature.

*Disease resistance*.—Leaves and fruit resistant but not immune to bacterial spot under growing conditions where bacterial spot infection is often very severe on susceptible genotypes. No bactericides were used in the development or evaluation of the instant cultivar. Evidence of bacterial spot infection was less than that of 'Winblo'. A commercial fungicide program was utilized in orchards used in the development and evaluation of the instant cultivar, thus no resistance to brown rot or scab, the other common diseases at Clarksville, Ark., were determined.

*Insect resistance*.—Insecticides were applied to orchards used in the development of the instant cultivar to control the common insects at the location including oriental fruit moth, plum curculio, stinkbug, tarnished plant bug, lesser peach tree borer, and greater peach tree borer. Therefore no insect resistance was determined in the testing of the instant cultivar.

Foliage/shoots/branches:

*Shoots*.—Smooth. Dormant-season shoot (branch): length 61.4 cm; diameter at base 0.7 cm; diameter at midpoint 0.5 cm; diameter at terminal 0.3 cm. Dormant-season shoot color Greyed-Purple Group (183A).

*Leaves*.—Simple, alternate, glabrous, lanceolate, petiolate, and deciduous. Venation pinnate; base acute; terminal or apex acuminate; margin serrated. Mature leaf size: length 15.4 cm; width midpoint 3.4 cm. Leaf serrations 4.3/cm. Mature leaf color: abaxial — Green Group (139B); adaxial — Green Group (139A). Young leaf color: abaxial — Yellow-Green Group (146C); adaxial — Yellow-Green Group (144A); anthocyanin not present on abaxial or adaxial side of young leaves on midrib or other location. Petiole diameter — mature leaf: 1.2 mm (average from five leaves). Petiole length — mature leaf: 1.0 cm. Leaf glands: reniform, average of 3 per leaf, located at base of leaf blade at top of petiole. Leaf glands are 0.07 cm in width and 0.11 cm in length.

*Buds*.—Number of leaf buds per 15 cm: 12, evenly distributed along the shoot. Number of flower buds per 0-15 cm from terminal: 16.2. Flower bud shape: rounded. Mature shoot internode length: base 1.8 cm, midpoint 1.6 cm, terminal 0.5 cm.

Bark (of mature trunk of tree):

*Color*.—Greyed-Green Group (198D).

*Texture*.—Rough.

Trunk:

*Diameter*.—12.9 cm (at 25 cm above ground level).

Flower buds: Dormant flower bud length 0.5 cm and diameter 0.2 cm and color Greyed-Green Group (197D); dormant buds swell and expand in late winter and increase in size during this expansion to fully open flowers.

Flowers: Bloom occurs prior to vegetative bud break; solitary to occasional double individual flowers at a single node; perfect; self-fertile. Flower depth: 21.7 mm (average of five measurements. Both male and female organs in each flower.

*Date of bloom*.—First, Julian 80 (March 20); Full, Julian 83 (March 23), one day after 'Loring'.

*Size*.—Diameter fully open 3.5 cm.

*Shape*.—Bowl shaped.

*Type*.—Showy.

*Density of flowers*.—16.2 flowers/8.5 inches (average of five measurements).

*Color*.—Adaxial: Red Purple Group (62D); abaxial: Red-Purple Group (62B).

*Petals per flower*.—5.8.

*Petal dimensions*.—Length 18.6 mm; width 16.3 mm.

*Petal shape*.—Apex-rounded, margin — entire (smooth), base — cuneate, overall — elliptic (round).

*Petal texture*.—Texture smooth both adaxial and abaxial surfaces — no pubescence.

*Length of pistil*.—1.7 cm. Pistils per flower — 1 (average of five measurements).

*Pistil color*.—Grayed green group 195D.

*Stamens*.—Average 46.2/flower with pollen present, fertile and abundant. Stamen position relative to flower petals — Stamens are erect while petals have a more gradual upward orientation.

*Sepals*.—Number per flower — 6 (average of five). Shape overall — ovate (non-fused), oblanceolate (fused). Length — 4.5 mm; Width — 3.9 mm. Apex — rounded. Texture — moderate pubescence on both sides. Base — cuneate. Margin — entire (smooth). Color — Upper (adaxial) — grayed purple group 185-B — Lower (abaxial) — red purple 60-A.

*Pollen*.—Grayed orange group 165B.

*Ovary*.—Pubescent. Color — grayed green group 195C.

Fruit:

*Size*.—Medium, avg. 183 g; diameter stem end 4.9 cm, equator 7.2 cm, blossom end 4.2 cm; length base to apex 6.6 cm.

*Shape*.—Round, symmetrical with no tip.

*Skin*.—Lightly pubescent (fuzzy), attractive; ground color Yellow-Orange Group (21B), with red blush (Red Group 46A) covering about 90% of surface on average.

*Flesh*.—Color Yellow-Orange Group (20A); freestone; melting texture, but very firm until fully ripe, "slow-melting". Firmness when measured by a fruit pressure tester (using a McCormick model FT327 fruit pressure tester, 11 mm diameter probe) on unpeeled fruit had average firmness value of 2.8 kg. Excellent eating quality; flavor sweet, and low acid.

*Pedicel length*.—1.1 cm.

*Pedicel diameter*.—0.4 cm.

*Pedicel color*.—Yellow-Green Group (144C).

*Ripe date*.—July 6 ('Julian 188') in west-central Arkansas; 'Loring' cultivar ripens 14 days later. Ripening of individual fruit is uniform.

*Tendency of pit to split*.—No split pits most years.

*Soluble solids*.—15.3%.

*Fruit juice pH*.—4.5; standard-acid cultivar 'Redhaven' 3.5.

*Fruit juice titratable acidity*.—0.24% expressed as malic acid; standard-acid cultivar 'Redhaven' 0.70%.

*Storage performance*.—Overall ranking for 0-3 weeks of storage for 'Souvenirs' was 3.7, the same as 'White County' and higher than 'Loring' (2.3) on a 5-point scale with 5 being exceptional storage. Notably, after three weeks of storage, 'Souvenirs' developed negligible mealiness (dry, gel texture) and maintained a high level of juiciness. When compared to the standard-melting peach cultivar 'Loring,' 'Souvenirs' fruit were substantially superior after 3 weeks of storage in terms of skin and flesh quality.

Pit/stone:

*Size*.—Length 3.3 cm; diameter (midpoint) 1.64 cm.

*Shape*.—Slightly oblong with deep furrowing and pitting.

*Color*.—Greyed-Orange Group (176A).

Kernel:

*Size*.—Length 1.6 cm; diameter varies with dryness of the kernel but is up to 0.5 cm.

*Shape*.—Almond.

*Color*.—Yellow Group (12C).

Uses: Fresh consumption, not evaluated for drying or other uses.

The Cultivar

The most distinctive features of the new cultivar are very firm fruit with slow-melting yellow flesh, early-mid season ripening, medium size, attractive appearance, high red skin color, excellent fruit quality, good flavor, and resistance to bacterial spot disease.

I claim:

1. A new and distinct cultivar of peach tree named 'Souvenirs,' substantially as illustrated and described herein.

* * * * *